United States Patent [19]

Lindsay, Jr. et al.

[11] 4,107,039
[45] Aug. 15, 1978

[54] DIALYSATE PREPARATION SYSTEM

[75] Inventors: Edward R. Lindsay, Jr., Clearwater; Stephen Mason Meginniss, III, St. Petersburg, both of Fla.

[73] Assignee: Extracorporeal Medical Systems, Inc., Pinellas Park, Fla.

[21] Appl. No.: 674,621

[22] Filed: Apr. 7, 1976

[51] Int. Cl.² ............................................. B01D 31/00
[52] U.S. Cl. ................................. 210/90; 137/505.47; 137/99; 210/136; 210/137; 210/321 B
[58] Field of Search ..................... 137/93, 99, 505.47; 210/137.22, 321 B, 90, 136

[56] References Cited

U.S. PATENT DOCUMENTS

| | | | |
|---|---|---|---|
| 1,202,403 | 10/1966 | Miller | 137/505.47 X |
| 2,804,089 | 8/1957 | Seifferle | 137/505.47 X |
| 3,032,056 | 5/1962 | Riley et al. | 137/505.47 X |
| 3,441,136 | 4/1969 | Serfass et al. | 210/137 X |
| 3,598,727 | 8/1971 | Willock | 137/99 X |
| 3,605,783 | 3/1966 | Pecker et al. | 137/93 |

OTHER PUBLICATIONS

Specification Sheet of Seattle Artificial Kidney Supply Co., copyright 1972.
"Human Factors in the Design of Artificial Kidney Machines," Published by The American Society of Mechanical Engineers, Nov. 1973.
"A Central System for the Continuous Preparation and Distribution of Hemodialysis Fluid," Grimsrud et al., vol. X, Trans. Amer. Soc. Art. & Int. Organs, 1964, p. 107.

*Primary Examiner*—Frank A. Spear, Jr.
*Attorney, Agent, or Firm*—Woodcock, Washburn, Kurtz & Mackiewicz

[57] ABSTRACT

A system continuously prepares dialysate by mixing water under pressure with concentrate to form dialysate under pressure. This dialysate is supplied on demand to a single patient station or to a plurality of patient stations. The pressure at which this dialysate is supplied to multiple patient stations is controlled so changes in the flow to one station will not change the pressure at which dialysate is supplied to other stations. A pressure regulator senses the pressure of the dialysate supplied to the patient stations and controls a regulator valve connected between the source of water under pressure and a proportioning pump which mixes this water with concentrate. The regulator includes a constant force spring assembly which provides a constant bias against the pressure in a sensing chamber over a range of linear movement of the pressure sensing element.

12 Claims, 4 Drawing Figures

DIALYSATE PREPARATION SYSTEM

BACKGROUND OF THE INVENTION

This invention relates to dialysate preparation systems and more particularly to a system for supplying dialysate under pressure to a patient station or to multiple patient stations.

Concentrate and water have been mixed in batch tanks to form dialysate for hemodialysis. Manual mixing in batch tanks is subject to error by the preparer and it is difficult to maintain sanitary conditions. Systems for continuously mixing concentrate and water have been used. U.S. Pat. No. 3,441,136 and 3,508,656 — Serfass et al. are examples of systems in which concentrate and water are continuously mixed for each individual patient.

The mixing can also be done continuously at a central location which supplies dialysate to a number of patient stations. "A central system for the continuous preparation and distribution of hemodialysis fluid," Grimsrud et al., Vol. X, *Trans. Amer. Soc. Artif. Int. Organs,* 1964, p. 107, describes such a central system. Dialysate must be supplied to each dialyzer at a constant pressure and at a temperature which is comfortable to the patient. In the aforesaid Grimsrud et al. system, a constant pressure is maintained by a head vessel. Further regulation is provided by a needle valve at each dialyzer. The temperature of the dialysate is controlled by two temperature controlled mixing valves at a central location.

The use of a central preparation system has advantageous of economy and reduced supervision in places such as a hospital where a number of patients are undergoing hemodialysis. There are two principal disadvantages of a central system. One disadvantage accompanies the use of a head vessel. The head vessels normally used in such systems are large and cumbersome. It is common to install such a vessel above the false ceiling of the hospital.

The use of a head vessel has the additional disadvantage of presenting a sanitation problem. Often, open vessels which are exposed to dust and bacteria in the air are used. Even closed head vessels have air pockets at the top thereof which expose the dialysate fluid to bacteria in the air. Often, head vessels have regions of little or no flow and in these regions, stagnant dialysate can become contaminated.

The other problem with prior central preparation systems arises because these systems heat the dialysate at the central location. A common dialysate temperature is not comfortable for all patients. Also, heating large quantities of dialysate at a central location requires high electrical power at that location and a special circuit must normally be installed to provide such power.

SUMMARY OF THE INVENTION

In accordance with this invention, dialysate is continuously prepared by mixing water under pressure with concentrate in a proportioning pump which produces dialysate under pressure. This dialysate can be supplied on demand to the patient station. In a multiple station system, the pressure at which the dialysate is supplied to the patient station is controlled by a pressure regulator. The dialysate is mixed cold at the central station and supplied to the patient stations where it is heated to the temperature desired by the individual patient.

Pressure regulation under the widely varying flow requirements of the patient stations is made possible by a unique regulator which controls a valve connected to a pressure sensing element. There is no flow interaction between the various units. The system provides almost instant response due to varying flow conditions, and it is insensitive to inlet water pressure changes.

In accordance with an important aspect of the invention, a constant force spring provides a constant bias for the pressure sensing element against water pressure over the entire range of movement of the pressure sensing element.

In accordance with another aspect of this invention, the cold preparation, mixing and monitoring of dialysate is carried out in a module which is separate from the patient station itself. This is important in both multiple patient station systems and in single patient systems.

The preparation system of this invention has the advantages of simple installation, reliable operation under widely varying patient demand conditions, clean, sanitary preparation without exposure of the dialysate and operation with normally available electrical distribution and plumbing systems. The system of this invention may be installed as a replacement for a number of existing single patient systems without changing the electrical or plumbing connections. Also, the system may be used to convert existing batch tank systems to proportioning systems.

The present invention provides a modular system in which the user can select the type of patient station which is desired. Two examples of patient stations which are usable with the present invention are those making use of coil or negative pressure dialyzers.

In accordance with another aspect of this invention, a unique mixing vessel supplied dialysate having the correct concentration even after prolonged periods during which there is no flow from a mixing vessel. This is important in both multiple station and single station dialysate preparation systems.

The foregoing and other objects, features and advantages of the invention will be better understood from the following more detailed description and appended claims.

DESCRIPTION OF THE PREFERRED EMBODIMENT

Figure 1:
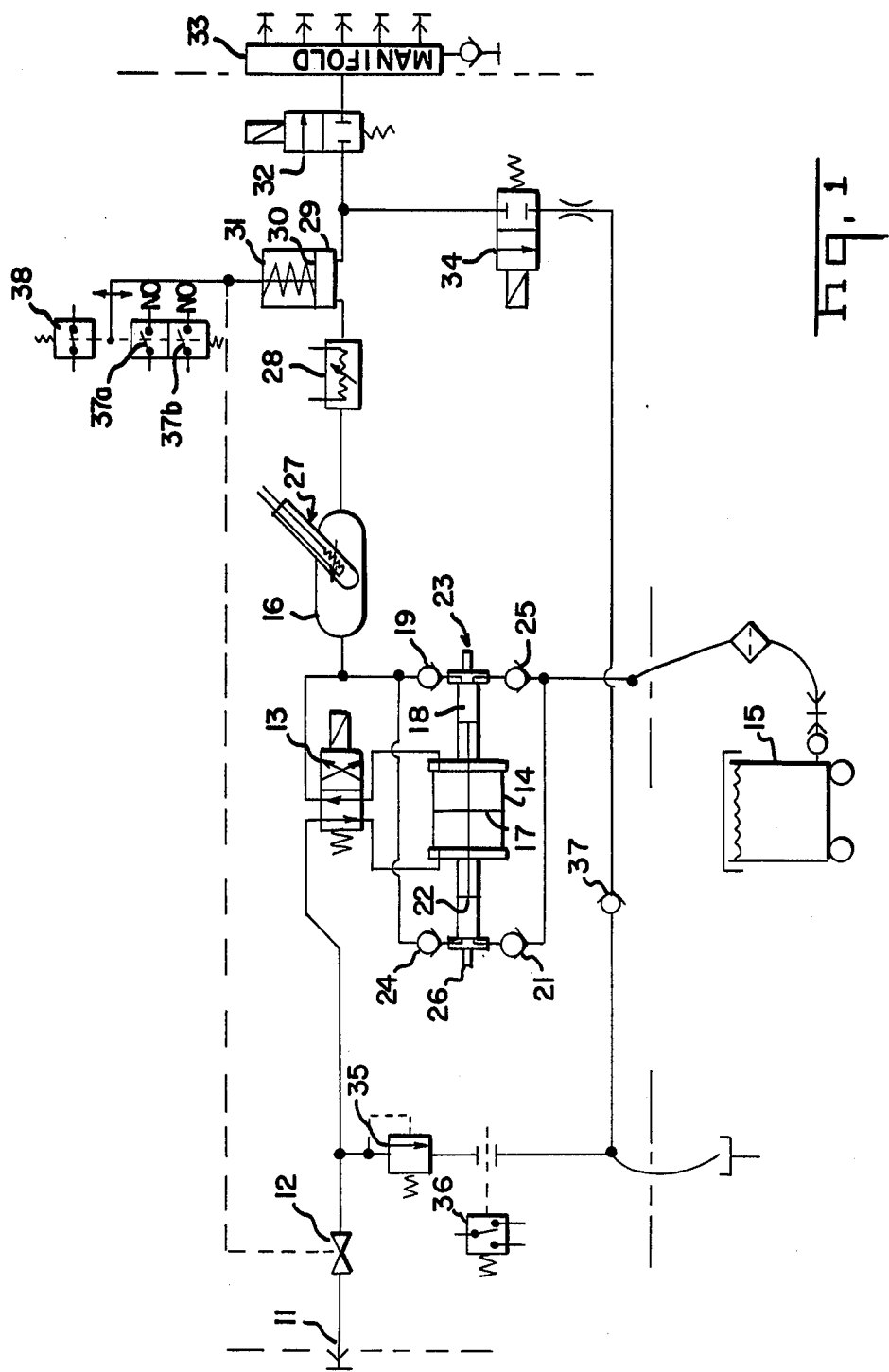
FIG. 1 shows a dialysate preparation system in accordance with this invention.

FIG. 1 shows a multiple station system. Water under pressure from a source 11 is supplied through a regulator valve 12 to the four-way pump valve 13 and the free-piston proportioning pump 14. The water is mixed with concentrate from the reservoir 15 in the correct proportions to form dialysate solution. The dialysate, still under the pressure regulated by the valve 12, is supplied to a closed mixing vessel 16.

The pump valve 13 and free-piston proportioning pump 14 are more fully described and claimed in copending application Ser. No. 547,625, filed Feb. 6, 1975. Briefly, the operation is as follows. With the valve 13 in the position shown, water pressure causes the large piston 17 in pump 14 to move toward the right. This forces a predetermined quantity of water on the right hand side of the piston 17 through the valve 13 and into the mixing vessel 16. Simultaneously, a predetermined volume of concentrate on the right hand side of the small piston 18 is forced through check valve 19 into the mixing vessel 16.

During this stroke of the piston, a precisely controlled volume of concentrate is drawn through the check valve 21 into the chamber on the left hand side of small piston 22. Similarly, a precisely controlled volume of water enters the large chamber to the left of piston 17.

When the piston 18 reaches the right hand extremity of its stroke, a magnetic switch 23 is actuated. This operates the valve 13 to its reverse position. With the valve in this position, water under pressure is applied to the right hand side of piston 17, thereby moving piston 17 toward the left. This forces a predetermined volume of water from the left hand side of the piston, through valve 13 to the mixing vessel 16. Simultaneously, a predetermined volume of concentrate is forced through check valve 24 to the mixing vessel 16. During this stroke of the piston, a precise volume of concentrate is drawn through the check valve 25 into the chamber on the right hand side of piston 18. When the piston reaches the left hand extremity of its stroke, a magnetic switch 26 is actuated. This operates the valve 13 to its other position, thereby reversing movement of the piston and repeating the cycle previously described.

The water driven double acting free-piston proportioning pump is an important feature of the system because it provides an instantaneous response to changing flow demand. The pump constantly proportions at the correct ratio under varying demand conditions.

In this manner, precise volumes of concentrate and water are mixed and delivered under pressure to the mixing vessel 16. A conductivity compensation thermistor probe 27 and a conductivity cell 28 monitor the concentration of the dialysate.

The dialysate is supplied to a constant pressure volume sensing chamber 29. A piston 30 is exposed to constant pressure in the sensing chamber and moves linearly in response to the changing volume in this chamber. The piston is connected by mechanical linkage to the regulator valve 12. Whenever the flow to the patient stations is not equal to the flow from the free-piston proportioning pump, the volume in the sensing chamber grows or shrinks due to the unequal flows. This volume change causes the piston to move the regulator valve which, in turn, varies the pump flow rate, until a balanced flow condition is established. A constant force spring assembly, indicated at 31, is connected to the piston to provide a constant bias against the pressure in the sensing chamber over the entire range of linear movement of the piston. Because of this, regardless of the volume of flow of the dialysate to the patient stations, the system is capable of maintaining a constant pressure. The dialysate is connected through an electrically operated shut-off valve 32 to a manifold 33. The patient stations are each connected directly to the constant pressure in the manifold 33. Each individual patient station has a heater for heating the dialysate to the desired temperature. Because the heaters are spread out, a normal electrical power distribution system is capable of handling the power requirements. Whereas a typical central dialysate preparation module requires a source of 220 volts power, the system of the present invention operates on 115 volts.

The drain valve 34 bypasses the dialysate to the drain when it is operated. When the central system is shut off or a power failure occurs, both the shut-off valve 32 and the drain valve 34 close, stopping all flow from the system. During normal operation, the shut-off valve 32 is open and the drain valve 34 is closed. However, when an alarm condition occurs, caused by an improper conductivity or pressure condition, for example, shut-off valve 32 is closed, stopping flow to the patient stations and drain valve 34 is opened to bypass the dialysate to drain.

In order to protect the system from excessive pressure and to prevent operation of the free-piston proportioning pump at a flow greater than its rated capacity, an overload (back pressure) valve 35 is provided.

Whenever the pump inlet water pressure rises above the predetermined level required for maximum rated flow, the back pressure regulating valve 35 opens to allow water to flow to drain. The back pressure valve 35 can pass great quantities of water, if required, to prevent the pump 14 inlet pressure from rising significantly above the aforementioned predetermined level. A flow sensing switch 36 is positioned in the drain path and is operated when water is flowing through the overload valve 35.

A check valve 37 is connected between the overload valve 35 and the drain valve 34 to prevent high pressure water from the overload valve being forced back to the patient stations if through inadvertence, the drain line becomes blocked. The flow switch 36 is connected with two switches 37a and 37b which are actuated by the piston 30, to provide an alarm indication if there is low water pressure or if the system is being overloaded because the patient stations are demanding more dialysate than can be supplied at the desired pressure. The switches are actuated when the volume sensing piston 30 is fully retracted; that is, there is low dialysate volume allowing the piston to move all the way to one extreme position.

A stop switch 38 is actuated when the volume sensing piston is fully extended to its other extreme position. The stop switch 38 shuts off electrical power to the system only after the regulator valve 12 has been closed to cut off water supply to the system. By using the valve 12 to shut off water completely when the system is shut down, the need for a separate inlet solenoid shut off valve is eliminated.

Figure 2:
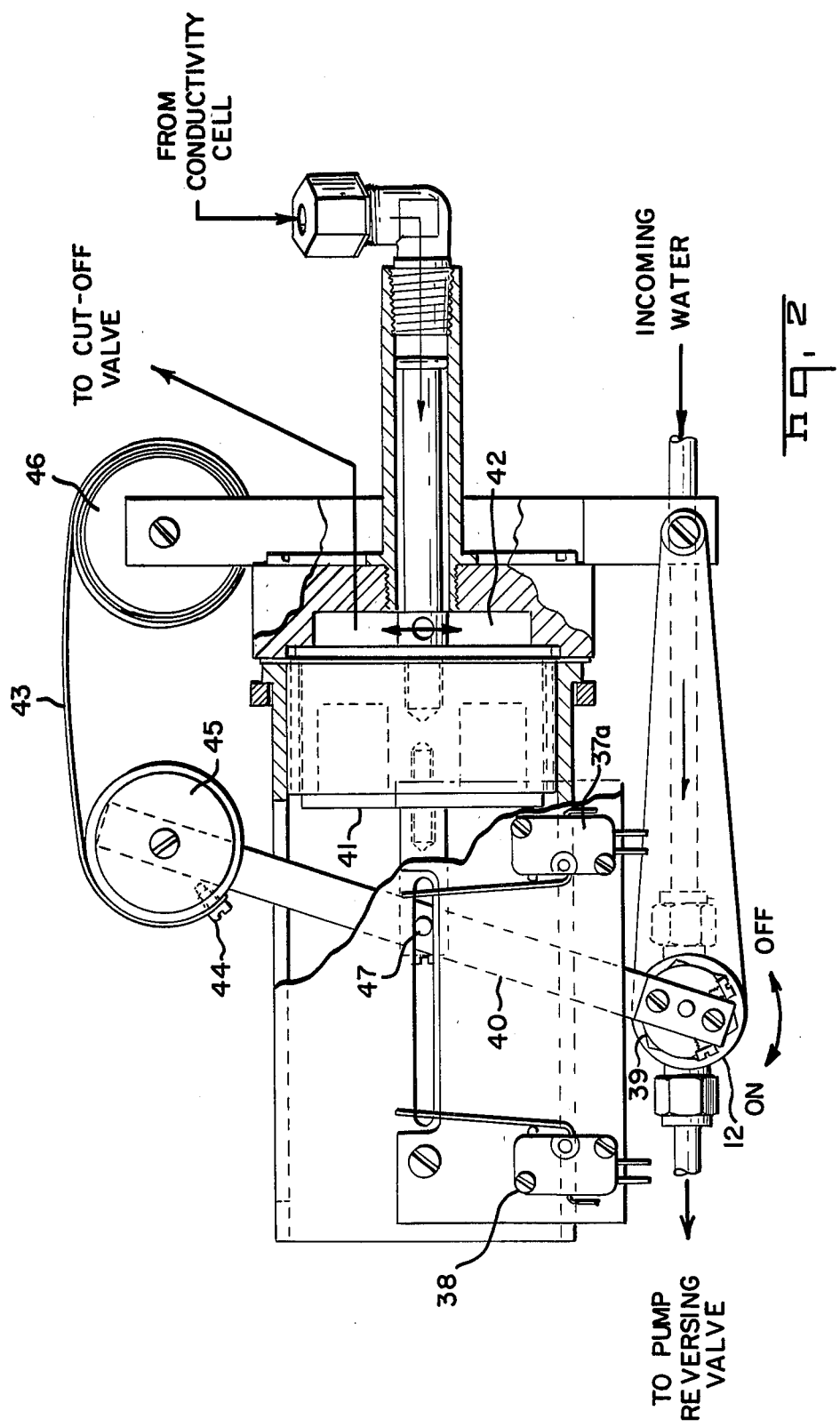
FIG. 2 shows the pressure regulator.

The constant pressure regulator is shown in FIG. 2. Water under pressure is supplied to a ball type regulator valve 39 having a regulator element which continuously changes the flow as the element is rotated. A linkage member 40 operates the regulator element in the valve 39. The ball valve reduces the high inlet pressure to the pressure required to meet flow demand. The pressure applied to the proportioning pump is the lowest possible for any given flow, thereby extending the wear life of the seals. A ball valve is particularly suitable for this purpose because its operating force (friction) is not significantly affected by changes in line pressure, thereby contributing to making the system output independent of inlet pressure.

The linkage member 40 is moved by a piston 41 which is exposed to dialysate pressure in the constant pressure volume sensing chamber 42. A relatively large volume of fluid is stored in the chamber 42. This storage capacity acts as an accumulator and provides flow on demand with no significant change in pressure. The pressure in the chamber 42 is maintained constant regardless of the position of the piston 41, which position varies the flow rate. This is required when several patient stations are being operated from a single dialysate source to prevent flow changes at one station from causing changes in flow to other stations.

Some dialyzers in use today require a considerable priming volume. The flow on demand capability of the system of this invention allows a user to prime a dialyzer very quickly without interfering with the operation of other stations. There are other situations in which extremely high flow rates are required and the present invention satisfies those requirements.

The piston 41 has a seal of the rolling diaphragm type. The use of such a seal has the advantage of presenting no moving friction and making a contaminant proof barrier. Also, there is no way for dust or dirt to get into the stream of dialysate because no surface which is exposed to the air is ever exposed to the dialysate. The rolling diaphragm allows the piston 41 to pass over narrow slots in the enclosing cylinder without leaking. If a standard seal, such as an "O"-ring or a cup seal was used, the linkage could not extend through the cylinder where the piston moves and the regulator would be larger. One type of rolling diaphragm which is suitable for use is shown in U.S. Pat. No. 2,849,026.

In order to provide a constant bias over the full range of travel of the piston 41, a constant force spring 43 is connected to the linkage 40. One end of the spring 43 is secured by the screw 44 to the non-rotating drum 45 on the linkage 40. The other end of spring 43 is wound on the rotating drum 46. As the linkage 40 moves, the spring 43 winds and unwinds on the drum 46 but it always applies the same force to the linkage. The linkage 40 has a pin 47 which rides in a slot in the casing to guide the linkage. The linkage system is designed so that the force on the piston is always a constant multiple of the spring force.

A stop switch 38 is positioned at one extreme end of travel to be actuated when the piston is fully extended. The switches 37a and 37b (not shown) are positioned at the other extreme position. They are actuated when the piston is at its extreme retracted position.

Figure 3:
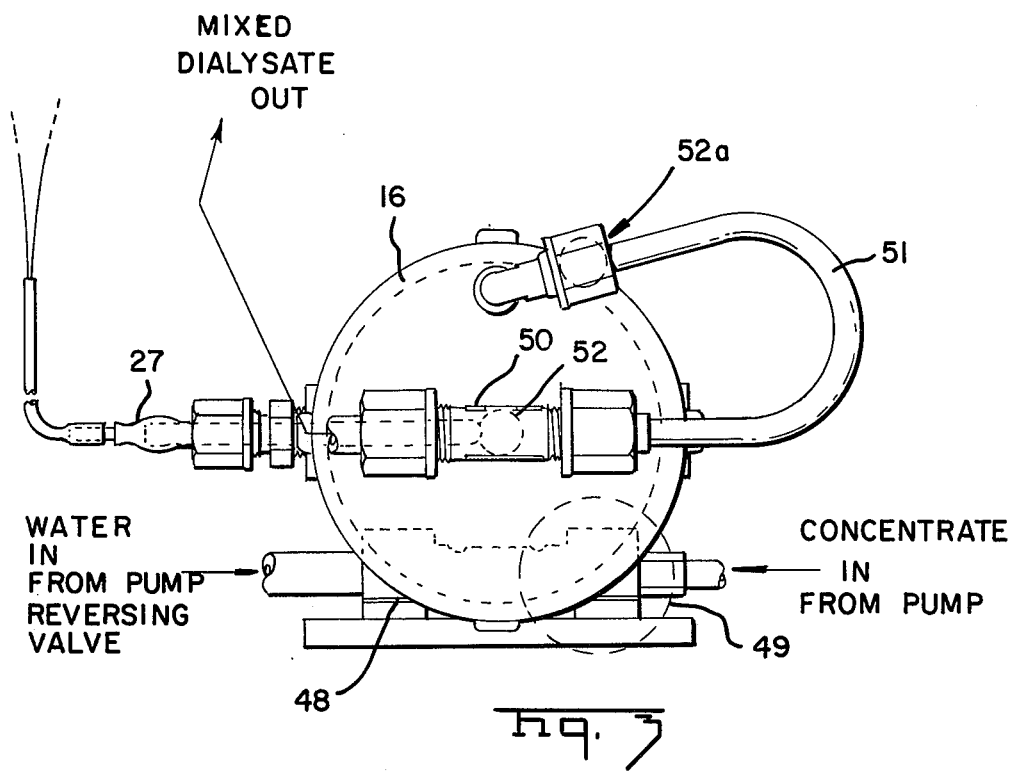
FIG. 3 shows the mixing vessel.

The mixing vessel 16 shown in FIG. 3 is a cylinder. A tee connector 48 is at the bottom of the flat cylindrical side which is away from the view. Concentrate is supplied to one inlet of tee 48 and water is supplied to the other inlet of the tee. A concentrate injection nozzle 49 in the tee 48 provides a high velocity continuous stream into the oncoming water thus causing turbulence to give good mixing. The mixing vessel 16 provides a large enclosed volume to allow the concentrate and water to form a homogeneous dialysate solution. The vessel 16 is enclosed so dialysate pressure is maintained.

The conductivity temperature compensation thermistor probe 27 mesures the temperature of the solution at the center of the cylinder. During periods when there is no dialysate flow out of the mixing vessel, the water rises to the top of the vessel and concentrate sinks to the bottom. However, the center of the cylinder has dialysate with the correct concentration. In order to take advantage of this, the outlet from the mixing vessel is taken from the center of the vessel. The tee 50 is connected at the center of the flat cylindrical face toward the viewer. The left hand of the tee is the outlet which is connected to the conductivity cell 28 (FIG. 1).

Because of the center location of the vessel outlet, it is necessary to provide a bleed line 51 to remove trapped air at the top of the vessel. The other end of air bleed line 51 is connected to the tee 50. An outlet restrictor inside the vessel at 52 creates a pressure drop which will force a small amount of fluid through the line 51. An orifice at 52a prevents a high dialysate flow through this line. The air bleed line allows air to escape quickly but restricts the flow of liquid to a small trickle. The amount of dialysate flowing through the line 51 is not sufficient to upset the maintenance of the correct concentration at the center of the cylinder. This unique arrangement of providing an outlet from the center of the cylinder and providing an air bleed line between the top of the vessel and the outlet has the advantage of always supplying dialysate at the right concentration even when flow resumes after a period of no flow.

Figure 4:
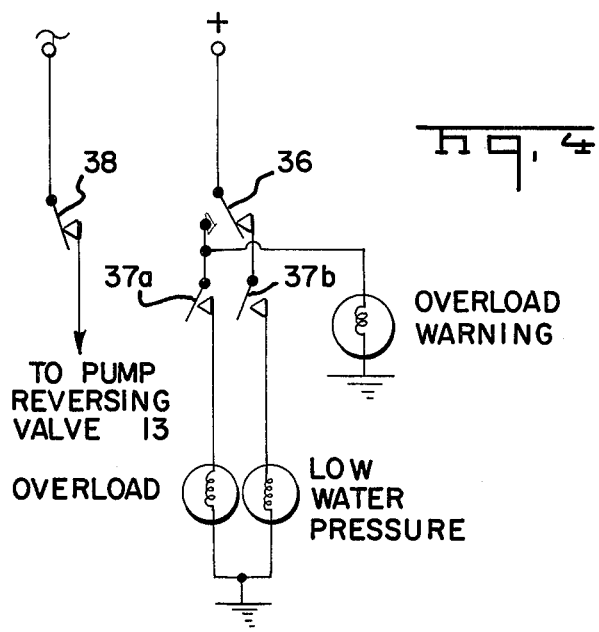
FIG. 4 is a simplified electrical schematic diagram.

FIG. 4 is a simplified electrical diagram showing the electrical connections to the components previously described.

The flow sensing switch 36 and the overload switch contacts 37a and 37b are connected to the overload, overload warning and low water pressure indicators and perform the following functions:

| | | OVERLOAD FLOW SENSING SWITCH 36 | |
|---|---|---|---|
| | | NO FLOW | FLOW |
| REGULATOR LOW OUTPUT PRESSURE SWITCHES 37a & 37b | OPEN REGULATOR OK | System OK no alarms | OVERLOAD warning audible & visual signals which can't be silenced. System continues to operate. |
| | CLOSED REGULATOR STARVED | Low WATER PRESSURE alarm-system shuts down. | OVERLOAD alarm - system shuts down. |

Power to the pump reversing valve 13 is applied through the contacts of the stop switch 38. This provides the important advantage of not shutting off power to the pump until the piston is fully extended, thereby completely shutting off the regulating valve 12. A situation in which water under pressure is applied to the system after power shut off is avoided.

While a multiple patient station has been described, certain principles of the invention are applicable to a single patient station. In this case, the pressure regulator shown in FIG. 2 is not used, but instead conventional pressure reducing valves are used. This provides a source of dialysate flow on demand but a variable pressure. As the patient load changes, the pressure regulators compensate for this changing condition and increase the flow through the proportioning pump. In this mode, there is a variation in pressure, but this is not significant for a single station because there is no other station flow to be affected by changing pressure. The important feature of this invention in this embodiment is the supply of dialysate on demand and at the correct concentration even after prolonged periods of non-use.

The appended claims are intended to cover the foregoing and further modifications which are within the spirit and scope of the invention.

What is claimed is:

1. A central system for continuously preparing dialysate for a plurality of dialysis patient stations comprising:

a source of water under pressure, a proportioning pump for mixing said water under pressure with concentrate to form dialysate under pressure, a regulator valve connected between said source of water and said proportioning pump, and volume sensing means connected between said proportioning pump and said patient station, said volume sensing means being connected to said regulator valve to control the pressure of the dialysate supplied to said patient station at a constant pressure for different flow rates of dialysate to said patient station.

2. The system recited in claim 1 wherein said proportioning pump comprises:

a double acting piston enclosed in a center cylinder, a pair of end cylinders with pistons therein disposed on either side of said cylinder, said water under pressure being alternately supplied to and discharged from said center cylinder as said piston reciprocates, said concentrate being alternately supplied to and discharged from said end cylinders as said piston reciprocates.

3. The system recited in claim 1 wherein said volume sensing means comprises:

a volume sensing chamber, a piston exposed to the pressure in said chamber and movable linearly in response to volume changes, said piston being connected to said regulator valve to regulate the water under pressure passing therethrough as said piston moves linearly.

4. The system recited in claim 3 further comprising:

a constant force spring assembly connected to said piston to provide a constant bias against the pressure in said sensing chamber over the entire range of linear movement of said piston.

5. The system recited in claim 4 further comprising:

a valve linkage connecting the regulator element of said valve with said constant force spring, said piston being connected to move said linkage, said linkage applying force to said piston in a constant multiple of spring force, and a shut-off switch positioned to be actuaged when said piston is fully extended, said shut-off switch being connected to shut off electrical power to said system only after said regulator valve has been closed to cut off water supply to said system.

6. The system recited in claim 5 further comprising:

switch means positioned to be actuated when said piston is fully retracted, said switch means being connected to indicate insufficient water pressure or overload flow condition.

7. The system recited in claim 6 wherein said switch means comprises:

first and second switch contacts, a back pressure valve connected between said regulator valve and said proportioning pump, said valve diverting water to drain when the pressure exceeds a predetermined level, a flow sensing switch which is actuated when water flows through said back pressure valve, said flow sensing switch being connected with one of the contact of said switch means to indicate a failing low water pressure of said source of water, said flow sensing switch being connected with the other contacts of said switch means to indicate that the flow of dialysate to said patient stations is greater than the amount which can be supplied by the system at the predetermined pressure.

8. The system recited in claim 1 further comprising:

a closed mixing vessel connected between said proportioning pump and said patient station, concentrate and water from said proportioning pump being supplied to said mixing vessel, and an outlet to said patient stations positioned in approximately the vertical center of said mixing vessel so that resumed flow of dialysate to said patient stations has correct concentration.

9. The system recited in claim 8 further comprising:

an air bleed line connected from the top of said mixing vessel to said outlet.

10. The system recited in claim 1 wherein said central system mixes dialysate at ambient temperature and wherein each patient station includes a heater for heating the dialysate to the temperature desired by the individual patient.

11. A system for continuously preparing dialysate for a dialysis patient station comprising:

a source of water under pressure, a proportioning pump for mixing said water under pressure with concentrate to form dialysate under pressure including a double acting piston enclosed in a center cylinder, and a pair of end cylinders with pistons therein disposed on either side of said cylinder, said water under pressure being alternately supplied to and discharged from said center cylinder as said piston reciprocates, said concentrate being alternately supplied to and discharged from said end cylinders as said piston reciprocates, means for controlling the pressure at which said water is supplied to said center cylinder, a closed mixing vessel connected between said proportioning pump and said patient station, concentrate and water from said proportioning pump being supplied to said mixing vessel, an outlet to said patient stations positioned in approximately the vertical center of said mixing vessel so that resumed flow of dialysate to said patient stations has correct concentration, and an air bleed line connected from the top of said mixing vessel to said outlet.

12. The system recited in claim 11 wherein said system mixes dialysate at ambient temperature and wherein each patient station includes a heater for heating the dialysate to the temperature desired by the individual patient.

* * * * *